(12) United States Patent
Nayar et al.

(10) Patent No.: US 6,923,939 B1
(45) Date of Patent: Aug. 2, 2005

(54) HEAT ACTIVATED MEMBRANE INTRODUCTION APPARATUS AND METHOD FOR SCREENING MATERIALS

(75) Inventors: Amit Nayar, Chicago, IL (US); Renxuan Liu, Chicago, IL (US); Richard R. Willis, Cary, IL (US); Eugene S. Smotkin, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 398 days.

(21) Appl. No.: 09/900,843

(22) Filed: Jul. 5, 2001

(51) Int. Cl.[7] .................. G01N 21/00; G01N 15/06; G01N 33/00; G01N 33/48; B01L 9/00

(52) U.S. Cl. ................ 422/104; 422/100; 422/101; 422/102; 422/103; 422/50; 422/55; 422/58; 422/68.1; 422/81; 422/83; 436/37; 436/43; 436/173; 436/181

(58) Field of Search .................. 436/37, 43, 173, 436/181; 250/288; 422/99–104, 50, 55, 58, 68.1, 81, 83

(56) References Cited

U.S. PATENT DOCUMENTS

| | | | | |
|---|---|---|---|---|
| 4,894,343 A | * | 1/1990 | Tanaka et al. | 435/285.2 |
| 5,032,508 A | * | 7/1991 | Naughton et al. | 435/32 |
| 5,135,850 A | * | 8/1992 | Prost | 435/29 |

(Continued)

FOREIGN PATENT DOCUMENTS

| | | | | |
|---|---|---|---|---|
| WO | WO 9710896 A1 | * | 3/1997 | B01J/19/00 |
| WO | WO 99/19724 | | 4/1999 | G01N/31/10 |
| WO | WO 00/29844 | | 5/2000 | G01N/33/00 |
| WO | WO 200105497 A1 | * | 1/2001 | B01J/19/00 |

OTHER PUBLICATIONS

Reddington, E.; Sapienza, A.; Gurau, G.; Rameshkrishnan, V.; Sarangapani, S.; Smotkin, E.S.; Mallouk, T.E. Science, 1998, 280, 1735.
Cong, P.; Doolen, R.D.; Fan, Q.; Giaquinta, D.M.; Guan, S.; McFarland, E.W.; Poojary, K.S.; Turner, H.W.; Weinberg, W.H. Agnew Chem, Int,Ed. 1999, 38, 4, 484.
Orschel, M.; Klein, J.; Schmidt,H–W.; Maier, W.F.; Agnew Chem, Int,Ed. 1999, 38, 18, 2791.
Soni, M.; Bauer, S.; Amy, J.; Wong.; Cooks, R.G. Anal. Chem. 1995, 67, 1409–1412.
Bauer, S.J.; Cooks, R.G. American Laboratory, 1993, 32.
Ovesen, C.V.; Stoltze, P.; Norskov, J.K.;.Campbell, C.T. Journal of Catalysis, 1992, 134, 445–468.
Jiang, C.J.; Trimm. D.L.; Wainwright, M:S. Applied Catalysis A: General, 1993, 93, 245–255.
Kotiaho, T.; Lauritsen, F.R.; Choudhury, T.K.; Cooks, R.G. Analytical Chemistry, 1991, 63, 18, 875 A.
Wong, P.S.H.; Cooks, R.G.; Cisper, M.E.; Hemberger, P.H. Environmental Science & Technology, 1995, 29, 215A.
Senkan, S. Agnew Chem Int. Ed., 2001, 40, 312–329.
Johnson, R.C.; Cooks, R.G.; Allen, T.M.; Cisper, M.E.; Hemberger, P.H. Mass Spectometry Reviews, 2000, 19, 1–37.
Idem, R.O.; Bakhshi, N.N.; Ind, Eng. Chem. Res, 1995, 34, 1548–1557.

*Primary Examiner*—Jill Warden
*Assistant Examiner*—Brian Sines
(74) *Attorney, Agent, or Firm*—John G. Tolomei; Frank S. Molinaro; Maryann Maas

(57) ABSTRACT

A process and apparatus for rapidly screening materials using, for example, mass spectrometry has been developed. More specifically, an array of materials on a fluid permeable support contained within a reaction cell having a semipermeable membrane can be rapidly screened for characteristics such as catalytic activity, selectivity, and adsorption and desorption properties.

34 Claims, 6 Drawing Sheets

U.S. PATENT DOCUMENTS

| | | | | |
|---|---|---|---|---|
| 5,183,744 A | * | 2/1993 | Kawamura et al. | 435/30 |
| 5,252,294 A | * | 10/1993 | Kroy et al. | 422/102 |
| 5,262,298 A | * | 11/1993 | Shipley et al. | 435/6 |
| 5,366,885 A | * | 11/1994 | Barranco, III | 435/6 |
| 5,589,136 A | * | 12/1996 | Northrup et al. | 422/102 |
| 5,604,132 A | * | 2/1997 | Capuano et al. | 436/52 |
| 5,849,208 A | * | 12/1998 | Hayes et al. | 216/94 |
| 5,959,297 A | | 9/1999 | Weinberg et al. | 250/288 |
| 5,965,092 A | * | 10/1999 | Chatterjee et al. | 422/130 |
| 6,008,016 A | * | 12/1999 | Walker et al. | 435/69.1 |
| 6,043,027 A | * | 3/2000 | Selick et al. | 435/4 |
| 6,063,633 A | * | 5/2000 | Willson, III | 436/37 |
| 6,068,393 A | * | 5/2000 | Hutchins et al. | 700/112 |
| 6,083,682 A | * | 7/2000 | Campbell et al. | 435/4 |
| 6,087,375 A | * | 7/2000 | Bridon et al. | 514/314 |
| 6,248,540 B1 | | 6/2001 | Weinberg et al. | 435/7.1 |
| 6,296,771 B1 | * | 10/2001 | Miroslav | 210/656 |
| 6,309,889 B1 | * | 10/2001 | Cutler et al. | 436/165 |
| 6,329,164 B1 | * | 12/2001 | Goodwin, Jr. | 435/29 |
| 6,358,479 B1 | * | 3/2002 | Frisina et al. | 422/131 |
| 6,395,552 B1 | * | 5/2002 | Borade et al. | 436/37 |
| 6,537,500 B1 | * | 3/2003 | Brenner et al. | 422/88 |
| 6,555,389 B1 | * | 4/2003 | Ullman et al. | 436/514 |
| 6,572,828 B1 | * | 6/2003 | Potyrailo et al. | 422/130 |
| 6,576,196 B1 | * | 6/2003 | Akporiaye et al. | 422/82.12 |
| 6,602,714 B1 | * | 8/2003 | Tagge et al. | 436/2 |
| 6,642,046 B1 | * | 11/2003 | McGarry et al. | 435/287.2 |

* cited by examiner

HEAT ACTIVATED MEMBRANE INTRODUCTION APPARATUS AND METHOD FOR SCREENING MATERIALS

STATEMENT REGARDING FEDERALLY SPONSORED RESEARCH OR DEVELOPMENT

This work was performed under the support of the U.S. Department of Commerce, National Institute of Standards and Technology, Advanced Technology Program, Cooperative Agreement Number 70NANB9H3035. The United States Government has certain rights in this invention.

FIELD OF THE INVENTION

The present invention relates to a process and apparatus for rapidly screening materials using, for example, mass spectrometry. More specifically, an array of materials on a fluid permeable support contained within a reaction cell having a semipermeable membrane can be rapidly screened for characteristics such as catalytic activity, selectivity, and adsorption and desorption properties.

BACKGROUND OF THE INVENTION

With the growth of combinatorial methodologies has come a need for rapid, high throughput, evaluation of combinatorially formed materials. Rapid screening methods that require only small quantities of material are increasingly in demand. Recently, Cong, P.; Doollen, R. D.; Far Q.; Gianquinta, D. M.; Guan, G.; McFarland, E. W.; Poojary, D. M.; Self, K.;

Turner, H. W.; Weinberg, W. H. Agnew Chem. Int. Ed. 1999, 38, 4, 484 reported a quadrupole mass spectrometer screening method for heterogeneous catalysis libraries in a sequential fashion. In Cong et al., each catalyst site of the library of catalysts was sequentially heated to a desired reaction temperature by a carbon dioxide laser. Reactant gases were then transported to the catalyst site through the annular section of a double concentric probe in a stagnation-flow manner.

A similar quadrupole mass spectrometer based screening technique was also reported in Orschel, M.; Klein, J.; Schmidt, H-W.; Maier, W. F.; Agnew Chem, Int, Ed. 1999, 38, 18, 2791, where the library consisted of an open structure where catalyst powders, prepared by the sol gel method, were placed in a spatially addressable configuration on a heated substrate. Screening was achieved by sequentially flowing a feed gas onto the surface of a catalyst spot through a capillary feed line and by withdrawing the products through another capillary line.

WO 99/19724 describes a method for rapid screening for activities and selectivities of catalysts by contacting potential catalysts at the test sites with a reactant stream to form product plumes. The product plumes were screened by passing a radiation beam to promote the formation of specified photoions and photoelectrons which are detected by microelectrode collection in situ in proximity to the respective test site.

WO 00/29844 describes a method of screening for activities and selectivities of catalyst libraries by contacting the catalysts at the test sites with a reactant stream to form product plumes. The product plumes are screened by translating a sample probe and/or the library to sample the product plumes and to conduct the plumes to a mass spectrometer where they are analyzed. One drawback to each of the above technologies is the extensive requirement for moving parts within the apparatus. Besides adding to the cost of the equipment, moving parts require a greater degree of maintenance, become a likely cause for mechanical failure, and, most importantly, may limit the speed with which the apparatus may be used to screen materials.

Still others have tried methods for screening libraries of materials using mass spectrometers; see U.S. Pat. No. 5,959, 297 B1 and U.S. 6,248,540 B1 where one embodiment shows a small volume created next to a library and filled with reactant gas. Selective IR heating of a thin substrate activates a library element of interest resulting in products which flow to a detector. U.S. Pat. Nos. 5,959,297 B1 and 6,248,540 B1 also state that a flow-through geometry can be employed.

The present invention provides a rapid screening method and apparatus that requires no moving parts and permits easy relative determination of a variety of characteristics. The present invention is a heat activated selective membrane introduction cell and detector for high throughput screening of materials such as inorganic solids, adsorbents, and heterogeneous catalysts. Advantages of the present invention include separating the effluent using a semipermeable membrane prior to conducting the effluent to a detector and using an array support as a thermal barrier to protect the semipermeable membrane from thermal degradation.

SUMMARY OF THE INVENTION

A purpose of the invention is to provide an apparatus for screening materials in an array where the apparatus has a cell having a first portion and a second portion and a fluid inlet and at least one fluid outlet. The first portion of the cell defines a passage and a window is positioned within the cell adjacent the first portion and in alignment with the passage. A fluid permeable array support is spaced apart from, but in alignment with, the window. A semipermeable membrane is adjacent the array support; and the fluid inlet and one fluid outlet are positioned on opposite sides of the combination of the array support and the semipermeable membrane. A specific embodiment of the apparatus further has a heat source in alignment with the window, and yet another specific embodiment of the apparatus has a detector in fluid communication with the fluid outlet.

Another purpose of the invention is to provide a process for screening materials in an array by first containing the array of materials within a cell and in alignment with a window in the cell. Then the array of materials is contacted with a feed fluid while sequentially selectively heating each of the materials in the array by impinging radiation that is passed through the window onto the selected material to form an effluent corresponding to the heated material. Each effluent is separated by flowing each effluent sequentially through a semipermeable membrane to form sequential sample streams. At least one component in each of the sequential sample streams is then detected. In a specific embodiment of the invention, the heating is accomplished by impinging radiation from a laser sequentially on the selected materials. In another specific embodiment of the invention, the detecting is accomplished by mass spectrometry. In yet another specific embodiment of the invention, at least one component of the feed fluid is isotope labeled. Measurements from the process can be used to determine information regarding a characteristic such as activity, selectivity, adsorption capabilities, desorption capabilities, mechanisms of reactions, kinetics of reactions, material formulation optimization, and process conditions optimization. The process of the present invention can be applied to screening an array of potential catalysts to determine the activity of the potential catalysts for the water gas shift reaction.

BRIEF DESCRIPTION OF THE DRAWINGS

FIGS. 1, 2, and 3 are generic figures and have been simplified by the deletion of a number of components of apparatus customarily employed but not specifically required to illustrate the performance of the present invention.

FIGS. 9 and 10 correspond with Example 3.

FIGS. 11 and 12 correspond to Example 5.

DETAILED DESCRIPTION OF THE INVENTION

Figure 1:
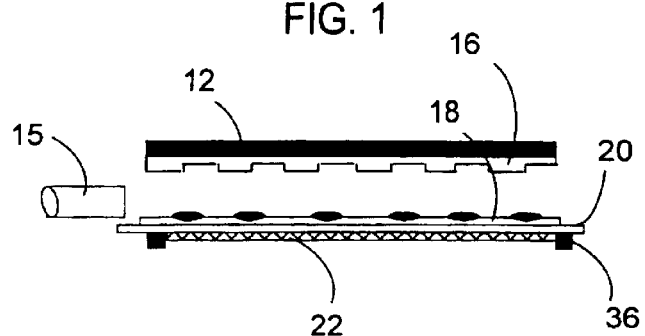
FIG. 1 is a partially exploded view of several elements contained within the cell of the apparatus of the present invention.

The apparatus of the present invention is designed for use in rapidly screening an array of multiple materials. The apparatus is particularly useful in combinatorial-type settings where a large number of materials have been synthesized combinatorially and are to be rapidly screened, to determine, for example, their effectiveness in a particular application. The apparatus allows for rapid high throughput of analyses so that a large number of materials can be screened in a minimum amount of time with a minimal amount of material. A major advantage of the apparatus is the lack of moving parts. Having no moving parts greatly facilitates the ease of operation and the speed of material screening. Practical applications of the apparatus and method are numerous and varied. For example, the apparatus and method of the present invention can be used to screen catalysts for activity and/or selectivity and adsorbents for adsorption capabilities and desorption capabilities. Mechanisms of reactions and kinetics of reactions can also be determined using the present invention. Also, deactivation of materials can be studied and material formulation or process conditions can be optimized.

The cell of the apparatus can be combined with any suitable detection technique such as optical methods, chromatographic methods, and combinations of technologies such as gas chromatography-mass spectrometry. Mass spectrometry was preferentially selected due to the sensitivity and speed of the technique. The preferred mass spectrometer is a quadrupole mass spectrometer. For ease of understanding, the description below will focus on mass spectrometry as the detection technique, but it must be emphasized that other detection techniques can be successfully employed.

In the following description, the apparatus of the invention will be presented first, followed by a description of the process of the present invention and examples of specific embodiments of the invention.

The cell of the invention is formed by a first portion and a second portion. The two portions can be separated for insertion of the array of materials within the reaction cell. When the cell is in use, the two portions are positioned to form a closed inner chamber which houses the array of materials and other structures discussed below. The two portions of the cell can be retained in position by one or more fasteners, such as a clamp, bolt, or the like. A seal can be employed between the two portions of the cell. Each portion may also have guide pins or guide holes to aid in alignment when closing the reaction cell. The cell also has one fluid inlet and at least one fluid outlet. For some applications it is preferred that the cell have two fluid outlets. The location of the fluid inlet and outlet(s) are discussed in greater detail below. When two fluid outlets are employed, for ease of operation, it may be advantageous to have the fluid inlet and at least one fluid outlet located within a single portion of the cell. The portions of the cell can be constructed of materials capable of withstanding the temperature of the application and inert with respect to the compounds used or generated in a given application. Suitable materials of construction include, without limitation, aluminum, stainless steel, ceramic, glass, quartz, and the like.

One portion of the reaction cell defines a passage which allows radiation to be directed into the reaction cell and impinge on the array of materials contained within the cell. A window is positioned within the reaction cell adjacent the passage to provide for a closed reaction chamber and yet allow the radiation to pass into the reaction cell. The window can alternatively be positioned and sealed within the passage itself. The window can be formed of any of a number of materials, and the material selected is dependent upon the particular application and the type of laser selected. The window is selected to be transparent to the wavelength of light provided by the laser. For example, when using a carbon dioxide laser, a zinc selenium window is preferred, when using an ultraviolet laser, a quartz window is preferred, and when using an infrared laser, a salt compound such as potassium bromide is preferred for the window. The material selected for the window can depend on the application, the reaction conditions, and the radiation being used.

It is preferred that the window be in contact with a seal such as an o-ring. The seal can be positioned between the reaction cell and the window and would serve the function of preventing fluid from exiting the reaction cell via the passage as well as holding the window in the correct position. It is further preferred that the passage and window be sized so that the array of materials contained within the reaction cell can be exposed to the laser without having to angle the overall laser unit. For example, the cross section of the passage is preferably equal to or larger than the footprint of the array of materials. The internal optics of the laser are used to direct the laser through the window to each of the individual members of the array.

Within the reaction cell and spaced apart from the window is a fluid permeable array support. The purpose of the array support is to hold the array of materials being investigated. The size and shape of the array support is not critical, and a variety of sizes and shapes can be employed. It is preferred that the size and/or shape of the array support be such that the radiation passing through the window is able to be directed at each of the materials on the support. As mentioned above, the array support is fluid permeable. It is preferred that the array support allows all the reactant and product compounds to pass through the support in contrast to the semipermeable membrane, discussed below, which selectively allows components to pass through. It is also preferred that the volume between the array support and the window be minimized to improve the sensitivity of the detector. In general, throughout the apparatus it is preferred that void volumes be minimized.

It is further preferred that the array support be of a material that allows for rapid heat dissipation. The radiation impinging upon the selected material of the array will cause the selected material to be heated to the desired temperature and the selected material may interact with the feed compound(s) to form an effluent. Some experimental conditions may routinely require high temperatures such as from about 200° C. to about 650° C. With the selected material being individually heated, it is preferred that the heat from the selected material is not conducted to neighboring materials in the array. Should other materials of the array become heated, error can be introduced into the data resulting from uncertainty as to which of the materials in the array caused a change detected in the effluent. Furthermore, heat transfer from the array support to the semipermeable membrane (discussed below) may limit the types of semipermeable membranes that may be employed. A large number of semipermeable membranes are not stable at higher temperatures. Therefore, another function of the array support is to act as a thermal barrier to protect the membrane from thermal damage and prevent convection of heat to neighboring materials within the array. A preferred array support is carbon paper, but other supports such as alumina may be employed. Carbon paper is readily commercially available as shown in the Gas Diffusion Electrodes and Catalyst Materials of E-Tek, Inc. The principal benefit of carbon paper as the array support is the quick dissipation of heat so that the heat from a selected material is not transferred to neighboring materials or to the membrane.

The array support may be spaced apart from the window in any reasonable manner. Devices such as a shelf, ledge, groove, or the like can be employed. It is preferred, however, that a spacer such as an o-ring be placed between the window and the array support, and it is most preferred that the spacer or o-ring contain notches or teeth so that fluid can flow freely around the spacer or o-ring and contact the array of materials.

It is preferred that the fluid contacts each of the materials in the array in a consistent manner. That is, each material in the array is preferably contacted with virtually the same space velocity of fresh fluid, regardless of the position of the material within the array, or the order in which the materials are screened. With variability in the amount of fresh feed contacting the different materials being minimized, the results of the analysis would be more comparable on a relative basis. Therefore, it is preferred that the reaction cell also contains a fluid diffuser or separator. The diffuser would be positioned between the fluid inlet and the array support so that the fluid entering the reaction cell passes through the diffuser prior to contacting the array of materials. The diffuser would operate to diffuse the fluid so that each material in the array would be exposed to a more consistent amount of fresh fluid. The diffuser would also define a transition from a higher pressure region at the fluid inlet to a lower pressure region. A higher pressure at the fluid inlet versus at the outlet of the diffuser drives the fluid through the diffuser so that the fluid is dispersed evenly upon exiting the diffuser. Various types of diffusers can be employed and are known in the art. A preferred diffuser is a microporous structure such as a frit. It is envisioned that the diffuser can be placed in the same orientation as the array support between the fluid inlet and the array support. Alternatively, the diffuser can be placed in an orientation perpendicular to the array support at the end of the reaction cell near the fluid inlet (see FIGS. 1 and 2). It is further preferred that the shape of the inlet and the outlet be such that the width of the inlet and the outlet be at least the size of the diameter of the passage in the first portion of the cell. The shape of the inlet and the outlet is preferably oval or rectangular, such as a slit. It is preferred that the diffuser is rectangular and of the same or slightly larger size as the cross section of the inlet and outlet. The fluid lines conducting fluid to the inlet and conducting fluid from the outlet can be heated.

A semipermeable membrane is positioned within the reaction cell adjacent to the array support. Depending upon the particular application, one or more of the products and/or reactants are prevented from passing through the membrane to be withdrawn through the fluid outlet located on the opposite side of the semipermeable membrane and array support from the fluid inlet. With the membrane being semi-fluid-permeable, the amount of reactant or product that is passed through the detection device is minimized and undesired components may be prevented from encountering the detection device. The membrane can be sized to be completely contained within the reaction cell or the membrane can be sized larger than the cross section of the cell so that the membrane can act as a seal between the first and second portions of the cell. The latter is especially preferred when the membrane is comprised of a material known to be used for sealing, such as silicone.

Semipermeable membranes are well known, and a wide variety of semipermeable membranes may be employed in the present invention. Depending upon the particular application, the membrane may be selected to retain selected components, or to allow only selected components to permeate through the membrane. For example, in reactions involving water, it may be preferable to select a hydrophobic membrane to prevent water from permeating through the membrane, especially if excess water is involved. The separated excess water could be removed from the reaction cell and not carried to the detection device where it may interfere with measurements. Some membranes are somewhat fragile and a thermally stable inert membrane support may be used. The membrane support is positioned between the membrane and the reaction cell. An example of a membrane support is a screen or macroporous structure.

Because of the array support being selected to rapidly dissipate the heat from the radiation source and thereby form a thermal barrier, semipermeable membranes that are not thermally stable at the conditions to which the solids are exposed may still be used in the present invention. For example, silicone rubber, a semipermeable membrane that is suitable for temperatures up to about 280 or 300° C. may be used in the present invention even where the material of the array will be exposed to temperatures of 500° C. and higher. With the array support being capable of rapidly dissipating the heat so that it is not conducted to the membrane, the membrane could be maintained at a stable temperature. Although the materials of the array will be individually heated to the higher temperature, the overall cell, including the membrane, can be maintained at a much lower temperature using heaters that are associated with the reaction cell. Any suitable heater may be employed, but it is preferred that the heater be incorporated into a cartridge that is incorporated into the cell. For example, the heaters can be cylindrical rods that are inserted through the portions of the cell to heat the interior cell volume. The maximum overall cell temperature is determined by the thermal stability of the semipermeable membrane. Optional thermocouples can be employed to monitor the temperatures of different locations within the cell.

In addition to being adjacent to the array support, the semipermeable membrane is positioned within the reaction cell so that it is between the fluid outlet of the second portion of the reaction cell and the fluid inlet of the first portion of the reaction cell. A preferred mode to retain the membrane in the desired position is a structure that can be part of the second portion of the reaction cell. For example, a ledge, shelf, or groove formed by the second portion of the reaction cell can be used to retain the membrane in the proper position within the reaction cell. Alternatively, a pressure fit between components of the reaction cell can be used to hold the membrane in position. The semipermeable membrane can further function as a pressure barrier between the pressure in the first portion of the reaction cell where the fluid contacts the array of materials and the second portion of the reaction cell where the components permeating the membrane are conducted away to a detector. If the detector is a mass spectrometer, the pressure after some of the fluid has permeated through the semipermeable membrane will be at a vacuum or near-vacuum pressure.

As mentioned briefly above, the present invention also allows a multiple pressure regime. For example, at the fluid inlet the pressure of the system may be $P_1$. On the opposite side of the diffuser from the fluid inlet, the pressure in the system may be $P_2$, which is less than $P_1$. This pressure difference on each side of the diffuser aids in driving the fluid through the diffuser. Finally, on the opposite side of the semipermeable membrane from the diffuser the pressure may be $P_3$, which is less than P2, and appropriate for the detector. Again, the pressure differences on opposite sides of the semipermeable membrane aid in driving components through the semipermeable membrane. The accommodation for a multiple pressure system allows a mass spectrometer to be a preferred detector since the mass spectrometer requires at least near-vacuum conditions.

Figure 2:
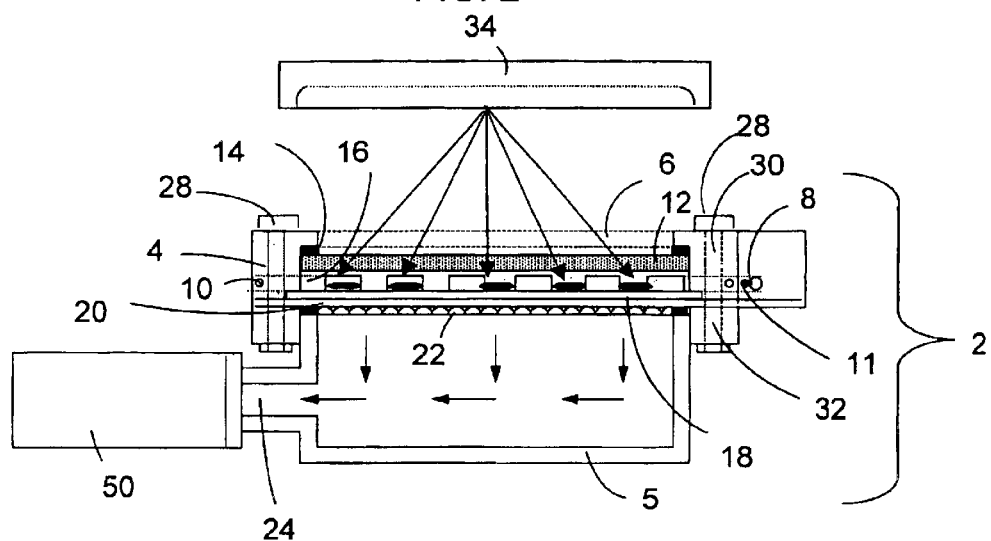
FIG. 2 is a generic assembled view of the apparatus of the present invention.

A specific embodiment of the invention is one where the array support is carbon paper and the semipermeable membrane is silicone. This specific embodiment is shown in FIG. 1 and FIG. 2. FIG. 1 is a partially exploded view of the internals of the cell of the apparatus while FIG. 2 shows an assembled view of the overall apparatus. The first portion 4 of cell 2 defines passage 6. The first portion 4 also contains fluid inlet 8 and fluid outlet 10. Between fluid inlet 8 and the internal volume of cell 2 is diffuser 11. Zinc selenium window 12 is held in position within reaction cell 2 by o-ring 14. O-ring 14 also seals window 12 and first portion 4 so that no fluid may pass through passage 6. Array support 18 is spaced apart from window 12 by toothed o-ring 16. Semipermeable membrane 20 is positioned within the reaction cell adjacent array support 18. Semipermeable membrane 20 is supported by membrane support 22. Membrane support 22 is held in place by o-ring 36. Heaters 15 (shown only in FIG. 1) are inserted through first portion 4 and provide heat to the interior of cell 2. The second portion 5 of cell 2 contains fluid outlet 24. The semipermeable membrane 20 is positioned at a location between fluid inlet 8 and fluid outlet 24. The first and second portions, 4 and 5 respectively, as well as semipermeable membrane 20, are maintained in position through bolts 28 that are threaded through holes 30 of the first portion 4, holes 32 of the second portion 5, and holes in the semipermeable membrane 20. Laser 34 is positioned in alignment with passage 6 and window 12.

Figure 3:
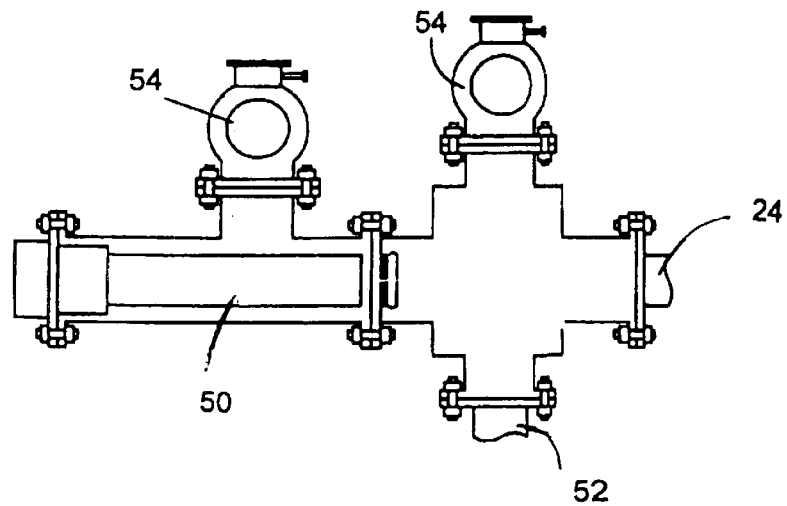
FIG. 3 shows a more detailed view of the fluid communication between the cell of the invention and a mass spectrometer.

Fluid outlet 24 is in fluid communication with mass spectrometer 50 as shown in FIG. 3. Optional calibration port 52 can be used in order to calibrate mass spectrometer 50. One or more pumps, 54, are present in order to achieve the proper pressure for mass spectrometer 50.

In general terms, the apparatus of the present invention would be used to rapidly screen an array of materials by sequentially selectively heating members of the array to a desired temperature while contacting the array of materials with a feed fluid introduced to the reaction cell though the fluid inlet. An effluent is generated, and one or more of the effluent components permeates through the semipermeable membrane and is removed from the cell through the fluid outlet. The fluid outlet is connected to a detector, for example, a mass spectrometer, which is used to measure the composition of the effluent or the quantity of one or more components of the effluent. The resulting measurements are used to determine a variety of information such as activity and/or selectivity, adsorption capabilities, desorption capabilities, mechanisms of reactions, kinetics of reactions, material formulation optimization, and process conditions optimization. The feed fluid can be compared to the measurements of the effluent to aid in determining information about the selected material. For example, if the quantity of a first component of the feed fluid is reduced as compared to the effluent, the selected material can have exhibited a capability for adsorption or conversion of the first component. If the quantity of a second component grows in the effluent as compared to the feed fluid, the selected material can have a capacity for catalyzing the generation of the second component. For relative comparisons, results of the measurement of the effluents can be compared.

The materials are preferably placed in the array support in the form of a circular spot of material. The selected material is heated to the desired temperature using the radiation source that is aligned with the passage and the window. A benefit of the present invention is that the radiation source can be controlled so that only the selected material is raised to the desired temperature and the remaining the materials in the array would be maintained at the temperature of the overall reaction cell. It is most preferred that the radiation source be a laser. For instance, a carbon dioxide laser would be directed through the passage, through the window, and focused to impinge on only the selected material. It is preferred that the focal distance of the laser be controlled to be located at a distance away from the surface of the selected material because the high energy density at an extremely fine point could pierce the array support and the membrane. The laser is de-focused so that the laser spot size coincides with the size of the surface of the selected material. The temperature of the region within the laser spot is controlled by the laser power.

For ease of understanding, the discussion below is directed to the specific embodiment of screening an array of materials for catalytic activity or selectivity as opposed to other information. The discussion is not meant to limit the scope of the invention, and one of ordinary skill in the art would readily understand how to adapt the invention to other embodiments. The assembled reaction cell is brought to a desired internal temperature using a heater associated with the reaction cell. Typically, that temperature will be below the reaction temperature of materials in the array. Suitable overall temperatures include but are not limited to from about 50° C. to about 250° C. Feed fluid is flowed through the fluid inlet in the first portion of the reaction cell. It is preferred that the feed fluid is passed through a diffuser so that the feed fluid is evenly distributed across the array of materials. Although the feed fluid is in contact with all of the materials in the array, the temperature of the reaction cell is preferably such that only a small amount of reaction will occur upon contact with each material in the array. The products of such reactions can be measured as background.

One material of the array is selected, and the radiation source is controlled to impinge at only the location of the selected material so that the remainder of the materials of the array are not exposed to the source radiation as discussed above. The selected material is heated by the radiation to a desired reaction temperature and can catalyze a reaction of the feed fluid thereby generating an effluent. It is preferred that the reaction cell have two fluid outlets. One fluid outlet may conduct those components not able to permeate the semipermeable membrane, and the other fluid outlet may conduct those components able to permeate the membrane. If there is only one fluid outlet, buildup of material unable to permeate the semipermeable membrane would necessitate periodic venting. In either case, at least one fluid outlet is in fluid communication with a detection device such as a mass spectrometer.

The detection device is used to measure the composition of the effluent or the concentration of a particular component of the effluent. Upon completion of the analysis of the effluent, the laser may be redirected to a second selected material of the array and the process repeated. Each material in the array would be sequentially heated by the laser to a reaction temperature to generate an effluent, and the detection device would-be used to analyze the effluent. Viewing the results of the measurements over the array of materials, or multiple arrays of materials allows for comparison of the performance of the materials in the array(s) and large numbers of materials may be screened to determine the most promising leads.

The present invention may be particularly beneficial in the class of reactions involving water as a reactant or a product. The semipermeable membrane can be selected to be hydrophobic or hydrophilic and thereby control where the water flows. With a hydrophilic membrane, the water can be selectively directed through the membrane and through the fluid outlet on the opposite side of the membrane from the feed fluid inlet. With a hydrophobic membrane, the water can be prevented from passing through the membrane and instead routed out of the reaction cell through a fluid outlet that is on the same side of the membrane as is the fluid inlet. This embodiment of the invention may be further demonstrated in the specific application of screening an array of catalysts for activity in a low temperature water-gas shift reaction.

The water-gas shift reaction may be expressed as:

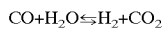

The water gas shift reaction is generally used to prepare high purity hydrogen or synthesis gas with a higher hydrogen to carbon monoxide ratio than the feed. The reaction is exothermic and its equilibrium favors hydrogen production as the reaction temperature is reduced. In general, commonly available feed fluids for the water-as shift reaction contains all four of the compounds involved in the reaction, carbon monoxide, water, hydrogen and carbon dioxide. To determine the activity of a catalyst in the reaction, a decrease in the amount of a reactant or preferably an increase in the amount of a product as compared to the feed fluid would need to be detected and measured. For example, in the water-gas shift reaction, it is preferable to measure the increase in the amount of carbon dioxide in the effluent as compared to the feed fluid. The apparatus and method of the current invention is particularly beneficial in this application because the membrane can be selected so that the water, which is typically present in relatively large quantities as compared to the other components, is separated from the component being monitored, the carbon dioxide.

The method as employed in the water-gas shift application would begin with a feed fluid containing water, carbon monoxide, hydrogen, a and carbon monoxide being introduced to the reaction cell via the fluid inlet. The reaction cell would be as described above in relation to FIG. 1 and would contain the array of materials to be screened. The array of materials, from about 2 to about 10 mg each, would be positioned on a carbon paper array support. Preferably, the feed fluid would pass through a diffuser to disperse the fluid evenly across the array of materials. The feed fluid would flow through the space created by a toothed o-ring positioned between the array support. A carbon dioxide laser would be directed through the zinc selenium window of the first portion of the reaction cell and at a first selected material on the array support. The laser would be adjusted so that the laser was slightly defocused at a selected material on the array support as discussed above. The selected material would be heated to the desired reaction temperature and may catalyze the water-gas shift reaction generating an effluent. Thermocouples can be used to monitor the reaction temperature of the materials in the array, and the laser can be calibrated so that adjustments in the intensity of the laser result in a predictable change in the temperature of the material. With the membrane being selected to be silicone rubber, which is hydrophobic, the water not consumed in the reaction would not pass through the membrane. Other components of the effluent, after passing through the membrane would be essentially water-free. Note that silicone rubber is a suitable membrane for separating water from other compounds, but is not stable at high temperatures (above about 280–300° C). With the unique design of the present apparatus, however, the silicone rubber membrane can be employed even though the reaction temperature of materials is substantially higher than the stability limitation of the silicone rubber. The controlled localized heating of the selected material with the laser in combination with the rapid heat dissipation and thermal barrier of the carbon paper array support operates to isolate the membrane from the higher temperatures, thus maintaining the membrane at the temperature of the reaction cell.

The portion of the effluent that passes through the membrane is removed from the reaction cell through a fluid outlet and passed through a conduit to a detector such as a mass spectrometer for measurement of one or more compounds. The process is repeated for each of the materials in the array. The process is rapid, and may be completed in as little as one minute per material in the array. The overall material results can be compared to each other to determine, on a relative basis or on an absolute basis, which material resulted in the greatest change in the amount of product. Each result can also be compared to the feed fluid.

It is contemplated that a catalyst conditioning or pretreatment process such as an activation process or a reduction process may proceed the screening process. For example, if the materials are catalysts, a reduction process may be employed to remove any metal oxides that may cause interference. The array in the reaction cell can be heated and a fluid purge can be used in the pretreatment process. Before the screening begins, the feed fluid may be passed through the cell for a period of time. Background measurements may be taken during the feed fluid purge.

It is further contemplated that the method of the present invention may be repeated one or more additional times with the results of each repetition being compared for information regarding the effect of contact with the feed fluid over time. For example, the relative deactivation of catalysts in an array may be rapidly screened with one or more repetitions of the method of the present invention and comparing the results from each repetition.

A computer can be used to control the feed fluid, the temperatures, the laser, and the detector. Furthermore, a computer can be used to collect the data from the detector, process the data and store the data.

In some applications, like the water-gas shift application above, a large amount of the compound being measured may already exist in the feed fluid. In the application above, feed fluids to water-gas shift reactions typically contain a large amount of carbon dioxide. The amount of catalyst being contacted with the feed fluid is generally small, thus the relative increased amount of carbon dioxide generated by the reaction may also be small, even if the catalyst is very active. The change in the concentration of carbon dioxide may be so small relative to the amount of carbon dioxide in the feed fluid that it may lie within the experimental error of the mass spectrometer. To overcome this difficulty, a specific embodiment of the present invention employs a technique commonly known as isotope labeling or isotope tracing. Isotope labeling makes use of stable isotopes, which are one of two or more nuclidic species of an element having an identical number of protons but a different number of neutrons. The isotopes differ in mass but are chemically the same element. In the present embodiment, the carbon monoxide may be labeled using the stable isotope $^{13}$C. to form $^{13}$CO which chemically reacts the same as $^{12}$CO. So, in the water-gas shift reaction catalyzed by the catalysts being screened, reactant $^{13}$CO would react to form product $^{13}$CO$_2$. Carbon dioxide that was not formed by the water-gas shift reaction, but that was present in the feed fluid would be unlabeled $^{12}$CO$_2$. Because of the different mass between $^{13}$CO$_2$, 45 a.m.u., and $^{12}$CO$_2$, 44 a.m.u., the mass spectrometer would detect them as two different peaks and be able to measure small changes in the labeled carbon dioxide in the presence of even large quantities of unlabeled carbon dioxide.

Isotope labeling can also be used in the present invention to determine the rates of a forward and backward reaction. For example in the water gas shift reaction, the forward reaction may be considered to be:

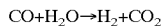

and the reverse reaction may be considered to be:

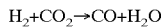

By labeling the CO in the feed as $^{13}$CO, not only can the amount of $^{13}$CO$_2$ formed by the forward reaction be measured, but the decrease in $^{12}$CO$_2$ consumed in the reverse reaction as well can also be measured. Similarly, increases in $^{12}$CO and water could be measured as generated by the reverse reaction. From these types of measurements, the rates of the forward and reverse reactions can be calculated using techniques known to those of ordinary skill in the art. Therefore, the present invention can also be employed to determine or screen reaction kinetics.

EXAMPLE 1

Three low temperature water gas shift catalysts containing copper, zinc, and aluminum oxides were prepared; the catalysts having the following molar ratios of metals:

TABLE 1

| Catalyst | Cu | Zn | Al |
|---|---|---|---|
| A | 2.5 | 4 | 1.5 |
| B | 2.5 | 4 | 1.5 |
| C | 1 | 7 | 1 |

Catalyst A was calcined at 400° C. for 3 hours and catalysts B and C. were calcined at 300° C. for 6 hours. The three catalysts were positioned in three different patterns on carbon paper array supports and evaluated using the apparatus and process of the present invention. The patterns consisted of a single row of the three catalysts, with the order of the catalysts in each array being different. A carbon dioxide laser was used as the radiation source and a quadrupole mass spectrometer was the detector. A feed fluid of hydrogen and carbon monoxide, with the hydrogen gas flow rate of 7 cc/m and the carbon monoxide gas flow rate of 0.5 cc/m, was purged through a water sparger at 76° C. and then contacted with the array of catalysts in the reaction cell. The general cell temperature was maintained at 150° C. using a heater. The laser was directed at the first catalyst of the first array and activated for a period of about 20 seconds at 6 percent power to achieve a reaction temperature of about 250° C. at the location of the first catalyst. The mass spectrometer was used to detect the generation of carbon dioxide as an indication of the relative activity of the catalyst for the water gas shift reaction. After about 300 seconds, the laser was directed at the second catalyst of the array and activated for a period of about 20 seconds. Again, the generation of carbon dioxide was detected by the mass spectrometer as an indication of the relative activity of the second catalyst. The process was repeated in the same manner for the third catalyst of the array. Water was prevented from flowing to the mass spectrometer by the silicone rubber membrane. The entire procedure was repeated for each of the arrays having the three catalysts in different patterns.

Figure 4:
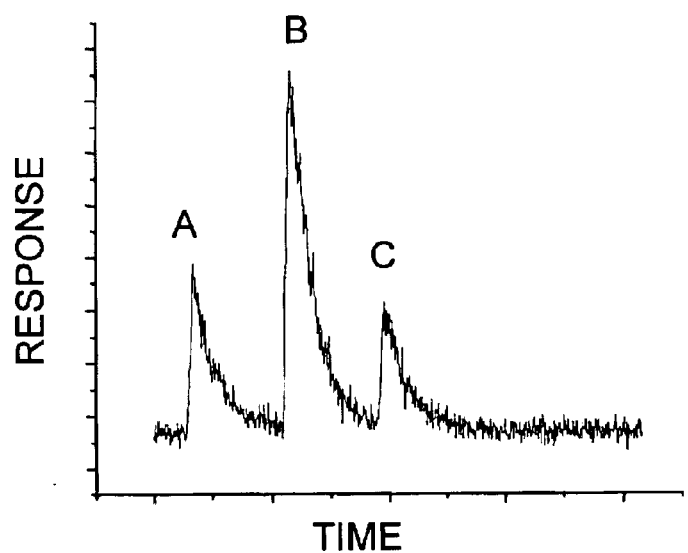
FIG. 4, FIG. 5, and FIG. 6 are plots of the mass spectrometer response at 44 a.m.u. (carbon dioxide) versus time for three arrays of catalysts, where each array contains the same three catalysts arranged in different patterns, corresponding to Example 1.
Figure 5:
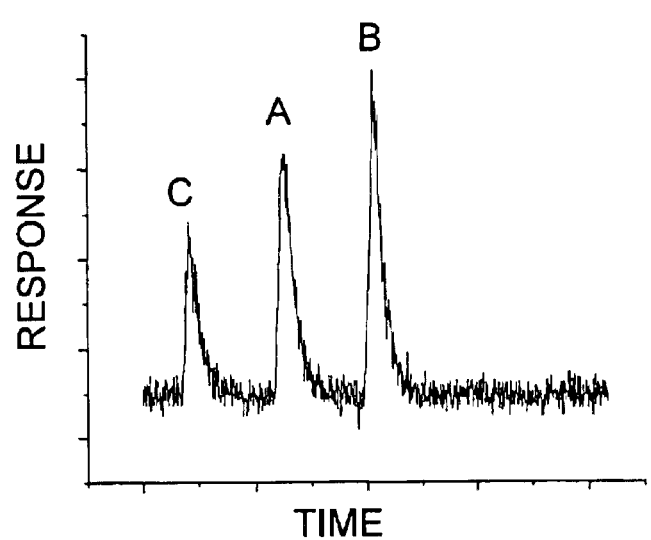
Figure 6:
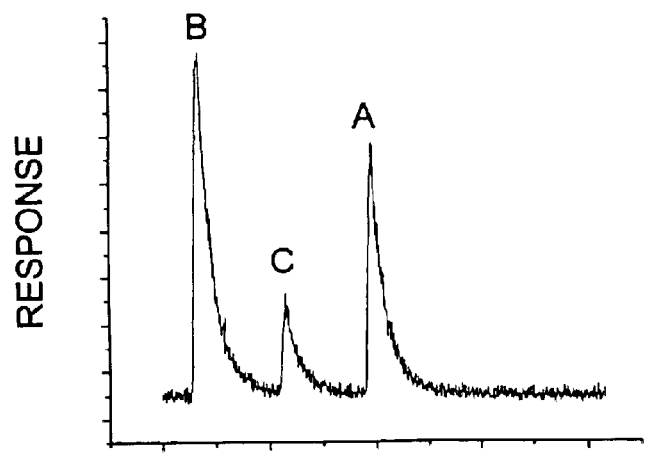

FIG. 4 shows the mass spectrometer response at 44 a.m.u. (carbon dioxide) versus time for the first array where the row of catalysts was arranged in the following pattern: A-B-C. The peak labeled "A" in FIG. 4 corresponds to the carbon dioxide detected when the active laser was directed at sample A. The peak labeled "B" in FIG. 4 corresponds to the carbon dioxide detected when the active laser was directed at sample B. The peak labeled "C" in FIG. 4 corresponds to the carbon dioxide detected when the active laser was directed at sample C. FIG. 5 shows the mass spectrometer response at 44 a.m.u. (carbon dioxide) versus time for the second array where the row of catalysts were arranged in the pattern C-A-B, and FIG. 6 shows the carbon dioxide detection versus time for the third array where the row of catalysts were arranged in the pattern B-C-A. These figures demonstrate that regardless of the position of the samples in the array, the process consistently showed that Catalyst B had the greatest generation of carbon dioxide, Catalyst C had the least generation of carbon dioxide, and that carbon dioxide generation of catalyst A fell between those of catalysts B and C. Therefore, the present invention is shown to be effective for screening the relative performance of a series of catalysts in general, and providing a ranking of the activity of a series of catalysts in the water gas shift reaction. The catalyst activity ranking of B>A>C as determined by the present invention was verified through independent micro-reactor testing.

EXAMPLE 2

Figure 7:
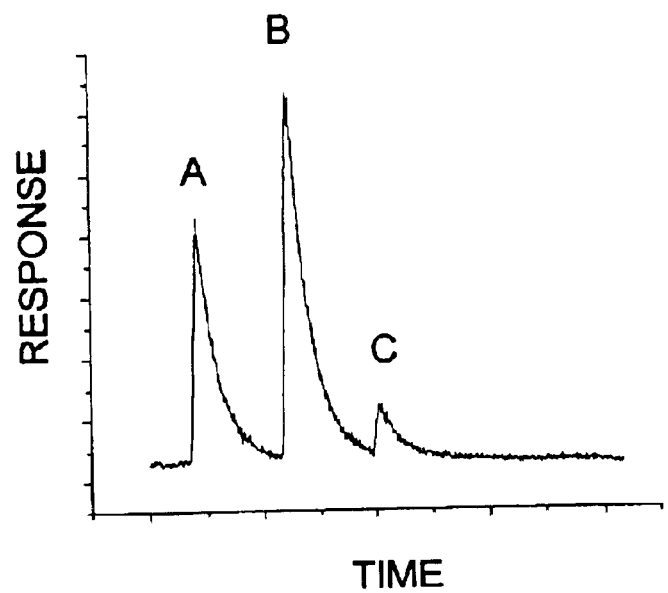
FIG. 7 is a plot of the mass spectrometer response at 44 a.m.u. (carbon dioxide) versus time for an array of three catalysts.
Figure 8:
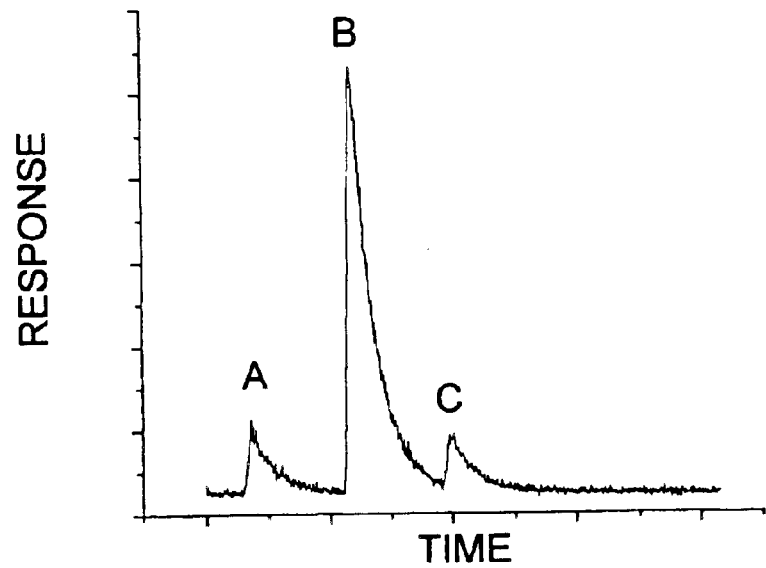
FIG. 8 is a plot of the mass spectrometer response at 44 a.m.u. (carbon dioxide) versus time for the same array of three catalysts re-screened after one hour according to Example 2.

An array of the same catalysts as in Example 1 where the row of three catalysts were arranged in the pattern, A-B-C was screened using the same procedure outlined above. FIG. 7 shows the mass spectrometer response at 44 a.m.u. (carbon dioxide) versus time resulting from this first iteration or run. One hour later, the identical array was re-screened using the same procedure. FIG. 8 shows the mass spectrometer response at 44 a.m.u. (carbon dioxide) versus time resulting from this second run. A comparison of the results of the first run with those of the second run shows the peak height of Peak A in FIG. 8 to be significantly less than the peak height of Peak A in FIG. 7, while Peaks B and C in FIGS. 7 and 8 remain relatively constant. The reduction in peak height of Peak A from FIG. 7 to FIG. 8 indicates deactivation of Catalyst A and stability thus far in Catalysts B and C.

EXAMPLE 3

Six bulk-supported low temperature water gas shift catalysts containing platinum on a ceria-zirconia support were prepared, labeled Catalysts D, E, F, G, H, I. Synthesis parameters were varied in the preparation of the six catalysts to investigate the effect of the parameters on the activity of the catalysts. The six catalysts were positioned in different patterns on two carbon paper array supports and evaluated using the apparatus and process of the present invention. The first pattern was a linear, single row, arrangement having the six catalysts in the single row. The second pattern was a 2×6 matrix of the six catalysts in each of two rows. A carbon dioxide laser was used as the radiation source and a quadrupole mass spectrometer was the detector. A feed fluid comprising hydrogen and carbon monoxide, with the hydrogen gas flow rate of 8 cc/m and the carbon monoxide gas flow rate of 0.5 cc/m, was purged through a water sparger at 76° C. and then contacted with the array of catalysts in the reaction cell of the present invention. The general cell temperature was maintained at 150° C. using a heater. The laser was directed at the first catalyst of the linear single-row array and activated for a period of about 20 seconds at 6 percent power to achieve a reaction temperature of about 250° C. at the first catalyst. Carbon dioxide was detected by the mass spectrometer as an indication of the relative activity of the catalyst. After about 300 seconds, the laser was directed at the second catalyst of the array and activated for a period of about 20 seconds. Again, carbon dioxide was detected by the mass spectrometer as an indication of the relative activity of the catalyst. The process was repeated in the same manner for the third through sixth catalyst of the array. Water was prevented from flowing to the mass spectrometer by the silicone rubber membrane. The entire procedure was repeated for the second array where the arrangement of the catalysts was in a 2×6 matrix where each row contained the same catalysts, but in different configurations.

Figure 9:
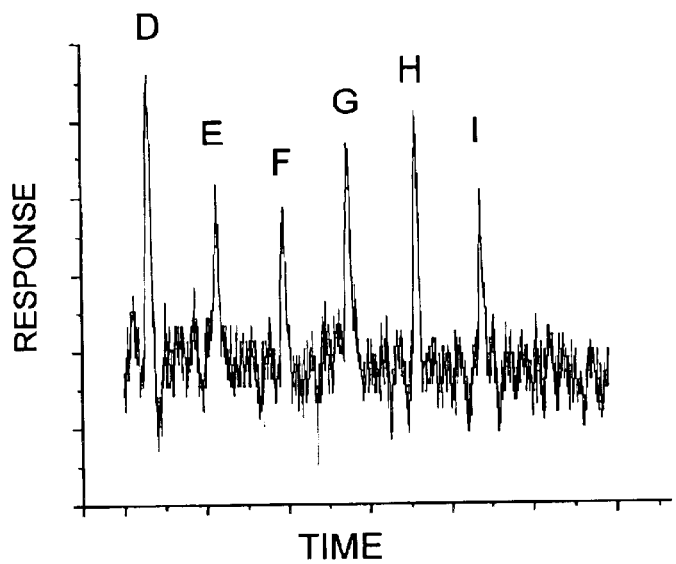
FIG. 9 is a plot of the mass spectrometer response at 44 a.m.u. (carbon dioxide) versus time for an array of six catalysts arranged in a linear row.
Figure 10:
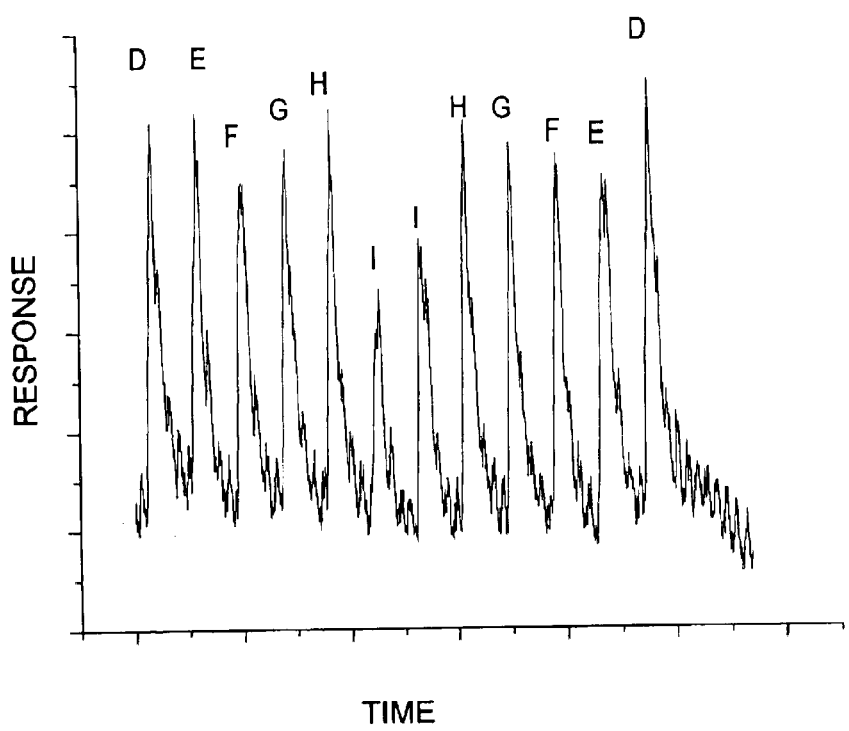
FIG. 10 is a plot of the mass spectrometer response at 44 a.m.u. (carbon dioxide) versus time for the array of six catalysts where the catalysts are replicate pairs arranged in a 2×6 matrix.

FIG. 9 shows the carbon dioxide detection versus time for the first array where the catalysts were arranged in a linear pattern. FIG. 10 shows the carbon dioxide detection versus time for the second array where the catalysts were arranged in a 2×6 matrix. The peak labels correspond to the carbon dioxide detected when the laser was directed at the catalyst of the same label. The catalysts were also evaluated through independent micro-reactor testing. The results of the micro-reactor testing at 250° C. are shown in Table 2.

TABLE 2

| Catalyst | D | E | F | G | H | I |
|---|---|---|---|---|---|---|
| Percent CO Conversion | 27 | 2 | 6 | 8 | 10 | 6 |

The ranking of the catalysts from most active (greatest CO conversion to $CO_2$) to least active compares quite well between FIG. 9 and the micro-reactor data in Table 2. FIG. 10 shows some variability.

EXAMPLE 4

Figure 11:
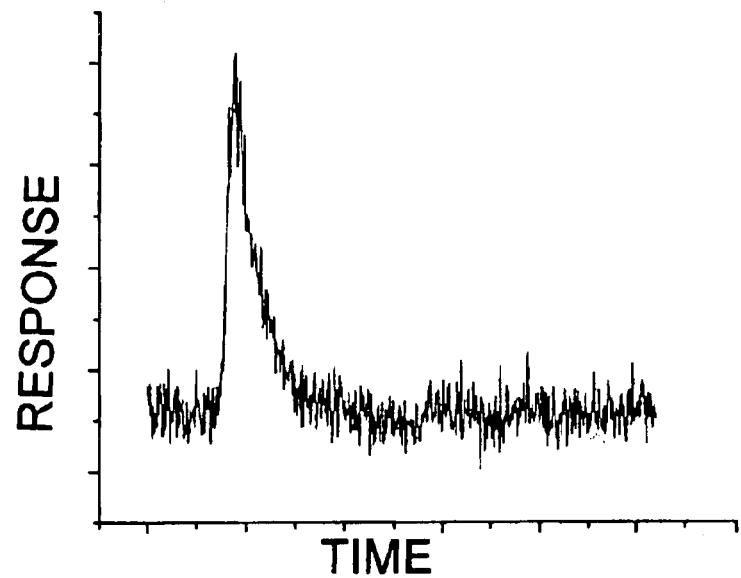
FIGS. 11 and 12 are plots of the mass spectrometer response at 44 a.m.u. (carbon dioxide) versus time for a single high temperature water gas shift catalyst where the catalyst was brought to a temperature of 375° C., and 400° C., respectively.
Figure 12:
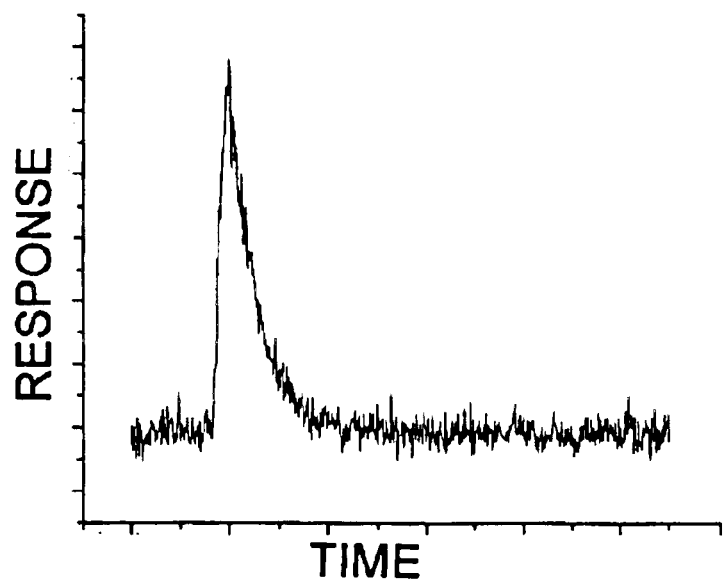

A commonly used high temperature water gas shift catalyst, $Fe_2O_3/Cr_2O_3$, was also evaluated with the present invention using the feed fluid as described above in Example 3. A single quantity of the catalyst was supported on carbon paper. The laser power was adjusted to bring the catalyst on the carbon paper to a temperature of 375° C. FIG. 11 shows the carbon dioxide detection versus time for the catalyst at 375° C. The experiment was repeated with the laser power adjusted to bring the catalyst to a temperature of 400° C. FIG. 12 shows the carbon dioxide detection versus time for the catalyst at 400° C. The resulting peaks in FIGS. 11 and 12 have the expected shape and the silicone membrane was not damaged by the catalysts exceeding the stable temperature of the membrane. No changes or deformations were observed on either the carbon paper or the silicone membrane. The array support successfully provided a thermal barrier for the silicone membrane, thereby allowing the catalysts to be at temperatures much higher than the thermal limit of the semi-permeable membrane.

EXAMPLE 5

The same catalysts as in Example 1, catalysts A, B, and C, were contacted with a feed fluid containing hydrogen, carbon dioxide, water, and isotope labeled carbon monoxide. The hydrogen gas flow rate was 8 cc/m, the isotope labeled carbon monoxide gas flow rate was 0.5 cc/m, and the carbon dioxide flow rate was 2.5 cc/m. The mixture was purged through a water sparger at 76° C. and then contacted with the array of three catalysts in the reaction cell. The general cell temperature was maintained at 150° C. The laser was directed at the first Catalyst, A, of the array and activated for a period of about 20 seconds at 6 percent power to achieve a reaction temperature of about 250° C. at the location of the first catalyst. The mass spectrometer was used to detect carbon dioxide at 44 a.m.u., carbon dioxide at 45 a.m.u. and water at 18 a.m.u. Increases in carbon dioxide at 45 a.m.u. would indicate the generation of isotope labeled carbon dioxide from the reaction of the isotope labeled carbon monoxide. Decreases in carbon dioxide at 44 a.m.u. would indicate the consumption of carbon dioxide in the reverse reaction to form water and carbon monoxide.

After about 300 seconds, the laser was directed at the second catalyst, B, of the array and activated for a period of about 20 seconds. Again, the mass spectrometer was used to monitor the effluent components listed above. The process was repeated in the same manner for the third catalyst, C, of the array with the effluent components monitored. Most of the water was prevented from flowing to the mass spectrometer by the silicone rubber membrane, but the amount that flowed into the mass spectrometer was measured.

Figure 13:
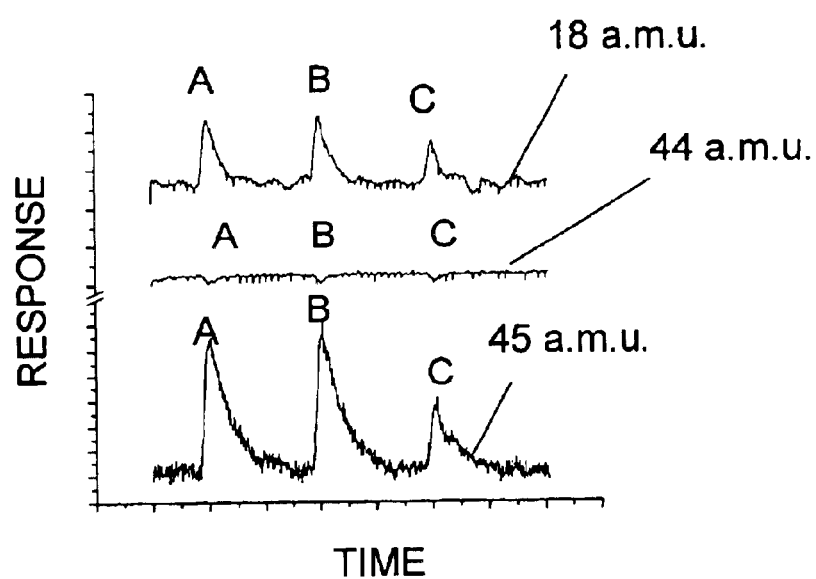
FIG. 13 is a plot of the mass spectrometer response for carbon dioxide at 44 a.m.u., carbon dioxide at 45 a.m.u., and for water at 18 a.m.u. versus time for an array of three catalysts, according to Example 6.

FIG. 13 shows the mass spectrometer response for carbon dioxide at 44 a.m.u., carbon dioxide at 45 a.m.u., and for water at 18 a.m.u. versus time for the array of catalysts, A, B, and C. The peak labeled "A" in FIG. 13 corresponds to the responses detected when the active laser was directed at sample A. The peak labeled "B" in FIG. 13 corresponds to the responses detected when the active laser was directed at Sample B. The peak labeled "C" in FIG. 13 corresponds to the responses detected when the active laser was directed at Sample C. From this collection of data, not only can the catalysts be screened and ranked according to activity by observing the generated levels of isotopic labeled carbon dioxide, but kinetic information such as the rates of the forward and reverse reactions can be calculated.

What is claimed is:

1. An apparatus for screening materials in an array comprising:
    a) a cell comprising a first portion and a second portion, said cell having a fluid inlet and at least one fluid outlet and said first portion defining a passage;
    b) a window positioned within the cell adjacent the first portion and in alignment with the passage;
    c) a fluid permeable array support spaced apart from, and in alignment with, the window wherein the array support has at least two locations for the window wherein the array support has at least two locations for supporting material;
    d) a semipermeable membrane adjacent the array support;
    e) a membrane support adjacent to the semipermeable membrane;
    f) said fluid inlet and one fluid outlet positioned on opposite sides of the combination of the array support and the semipermeable membrane; and
    g) a location selective heat source in alignment with the windows, wherein said location selective heat source sequentially heats the materials at the locations of the array support.

2. The apparatus of claim 1 further comprising a detector in fluid communication with the fluid outlet.

3. The apparatus of claim 1 further comprising at least one fastener connecting the first portion and the second portion of the reaction cell.

4. The apparatus of claim 1 further comprising a seal positioned within the reaction cell between the first portion of the cell and the window.

5. The apparatus of claim 1 further comprising a spacing support positioned between the window and the array support.

6. The apparatus of claim 5 wherein the spacing support is a toothed support.

7. The apparatus of claim 1 wherein the array support and the semipermeable membrane are comprised of different materials.

8. The apparatus of claim 1 further comprising at least one heater in contact with the cell.

9. The apparatus of claim 1 wherein the fluid inlet and one fluid outlet are located in the first portion of the cell while a second fluid outlet is located in the second portion of the cell.

10. The apparatus of claim 1 wherein the cell contains two fluid outlets where the fluid outlets are on opposites sides of the combination of the array support and the membrane.

11. The apparatus of claim 1 wherein the heat source is a radiation source.

12. The apparatus of claim 2 wherein the detector is a mass spectrometer.

13. The apparatus of claim 12 wherein the mass spectrometer is a quadrupole mass spectrometer.

14. The apparatus of claim 1 wherein the semipermeable membrane is hydrophobic.

15. The apparatus of claim 14 wherein the semipermeable membrane is silicone rubber.

16. The apparatus of claim 1 wherein the array support is selected from the group consisting of carbon paper and alumina.

17. The apparatus of claim 2 wherein the detector is connected to a microprocessor.

18. The apparatus of claim 1 wherein the heat source is connected to a microprocessor.

19. An apparatus for screening materials in an array comprising:
    a) a cell comprising a first portion and a second portion, said cell having a fluid inlet and at least one fluid outlet and said first portion defining a passage;
    b) a window positioned within the cell adjacent the first portion and in alignment with the passage;
    c) a fluid permeable array support spaced apart from, and in alignment with, the window;
    d) a semipermeable membrane adjacent the array support;
    e) a membrane support positioned within the cell adjacent to the semipermeable membrane; and
    f) said fluid inlet and one fluid outlet positioned on opposite sides of the combination of the array support and the semipermeable membrane.

20. The apparatus of claim 19 further comprising a detector in fluid communication with the fluid outlet.

21. The apparatus of claim 19 further comprising a seal positioned within the reaction cell between the first portion of the call and the window.

22. The apparatus of claim 19 further comprising at least one heater in contact with the cell.

23. An apparatus for screening materials in an array comprising:
    a) a cell comprising a first portion and a second portion, said cell having a fluid inlet and at least one fluid outlet and said first portion defining a passage;
    b) a window positioned within the cell adjacent the first portion and in alignment with the passage;
    c) a fluid permeable array support spaced apart from, and in alignment with, the window;
    d) a dispersion structure positioned between the fluid inlet and the array support;
    e) a semipermeable membrane adjacent the array support; and
    f) said fluid inlet and one fluid outlet positioned on opposite sides of the combination of the array support and the semipermeable membrane.

24. The apparatus of claim 23 further comprising a detector in fluid communication with the fluid outlet.

25. The apparatus of claim 23 further comprising a seal positioned within the reaction cell between the first portion of the cell and the window.

26. The apparatus of claim 23 further comprising at least one heater in contact with the cell.

27. The apparatus of claim 23 further comprising a membrane support positioned within the cell adjacent to the semipermeable membrane.

28. An apparatus for screening materials in an array comprising:
   a) a cell comprising a first portion and a second portion, said cell having a fluid inlet and at least one fluid outlet and said first portion defining a passage;
   b) a window positioned within the cell adjacent the first portion and in alignment with the passage;
   c) a fluid permeable array support spaced apart from, and in alignment with, the window;
   d) a semipermeable membrane adjacent the array support;
   e) said fluid inlet and one fluid outlet positioned on opposite sides of the combination of the array support and the semipermeable membrane; and
   f) a detector in fluid communication with the fluid outlet and a calibration port located between the fluid outlet and the detector.

29. The apparatus of claim 28 further comprising a seal positioned within the reaction cell between the first portion of the cell and the window.

30. The apparatus of claim 28 further comprising at least one heater in contact with the cell.

31. The apparatus of claim 28 further comprising a membrane support positioned within the cell adjacent to the semipermeable membrane.

32. The apparatus of claim 28 further comprising a dispersion structure positioned between the fluid inlet and the array support.

33. An apparatus for screening materials in an array comprising:
   a) a cell comprising a first portion and a second portion, said cell having a fluid inlet and at least one fluid outlet and said first portion defining a passage;
   b) a window positioned within the cell adjacent the first portion and in alignment with the passage;
   c) a fluid permeable array support spaced apart from, and in alignment with, the window wherein the array support has at least two locations for supporting material;
   d) a dispersion structure positioned between the fluid inlet and the array support;
   e) a semipermeable adjacent the array support;
   f) said fluid inlet and one fluid outlet positioned on opposite sides of the combination of the array support and the semipermeable membrane; and
   g) a location selective heat source in alignment with the window, wherein said location selective heat source sequentially heats the material at the location; of the array support.

34. An apparatus for screening materials in an array comprising:
   a) a cell comprising a first portion and a second portion, said cell having a fluid inlet and at least one fluid outlet and said first portion defining a passage;
   b) a window positioned within the cell adjacent the first portion and in alignment with the passage;
   c) a fluid permeable array support spaced apart from, and in alignment with, the window wherein the army support has at least two locations for supporting material;
   d) a semipermeable membrane adjacent the array support;
   e) said fluid inlet and one fluid outlet positioned on opposite sides of the combination of the array support and the semipermeable membrane;
   f) a location selective heat source in alignment with the window, wherein said location selective heat source sequentially heats the material at the locations of the array support; and
   g) a detector in fluid communication with the fluid outlet and a calibration port located between the fluid outlet and the detector.

* * * * *

UNITED STATES PATENT AND TRADEMARK OFFICE
CERTIFICATE OF CORRECTION

PATENT NO.    : 6,923,939 B1
DATED         : August 2, 2005
INVENTOR(S)   : Amit Nayar et al.

It is certified that error appears in the above-identified patent and that said Letters Patent is hereby corrected as shown below:

Column 15,
Lines 30-31, delete "the window wherein the array support has at least two locations for".
Line 40, replace "windows" with -- window --.
Line 41, replace "materials" with -- material --.

Column 16,
Line 38, replace "call" with -- cell --.

Column 18,
Line 6, after "semipermeable" insert -- membrane --.
Line 12, replace "location;" with -- locations --.
Line 22, replace "army" with -- array --.

Signed and Sealed this

Twenty-eighth Day of March, 2006

JON W. DUDAS
*Director of the United States Patent and Trademark Office*